United States Patent [19]
Adam-Molina

[11] Patent Number: 4,544,748
[45] Date of Patent: Oct. 1, 1985

[54] INTERMEDIATES FOR MEFLOQUIN
[75] Inventor: Solange Adam-Molina, St. Louis, France
[73] Assignee: Hoffmann-La Roche Inc., Nutely, N.J.
[21] Appl. No.: 525,341
[22] Filed: Aug. 22, 1983
[30] Foreign Application Priority Data
Sep. 10, 1982 [CH] Switzerland ............................ 5393/82
[51] Int. Cl.$^4$ .................... C07D 405/14; C07D 405/06
[52] U.S. Cl. ...................................... 546/167; 546/176
[58] Field of Search .................................. 546/176, 167

Primary Examiner—Glennon H. Hollrah
Assistant Examiner—D. B. Springer
Attorney, Agent, or Firm—Jon S. Saxe; Bernard S. Leon; William G. Isgro

[57] ABSTRACT

A process for the preparation of mefloquin and its physiologically compatible acid addition salts by reacting 6-phthalimido-1-hexene with a 4-halo-2,8-bis-(trifluoromethyl)-quinoline in the presence of a base, epoxidizing the resulting N-[6-<2,8-bis-(trifluoromethyl)-4-quinolyl>-5-hexenyl]-phthalimide to give N-[4-{3-<2,8-bis-(trifluoromethyl)-4-quinolyl>-2-oxiranyl}-butyl]-phthalimide, treating the latter with hydrazine hydrate and, where applicable, converting the product into an acid addition salt as well as intermediates obtained in this process.

2 Claims, No Drawings

INTERMEDIATES FOR MEFLOQUIN

BRIEF SUMMARY OF THE INVENTION

The invention relates to 4-quinoline derivatives and their preparation. In particular, it relates to N-[6-<2,8-bis-(trifluoromethyl)-4-quinolyl>-5-hexenyl]-phthalimide and N-[4-{3-<2,8-bis(trifluoromethyl)-4-quinolyl>-2-oxiranyl}-butyl]-phthalimide and their preparation as well as the conversion of the latter into mefloquin and its physiologically compatible acid addition salts.

DETAILED DESCRIPTION OF THE INVENTION

The invention relates to 4-quinoline derivatives and their preparation. In particular, it relates to N-[6-<2,8-bis-(trifluoromethyl)-4-quinolyl>-5-hexyl]-phthalimide and N-[4-{3-<2,8-bis(trifluoromethyl)-4-quinolyl>-2-oxiranyl}-butyl]-phthalimide and their manufacture as well as the conversion of the latter into mefloquin and its physiologically compatible acid addition salts.

Mefloquin, d, 1-erythro-alpha-(2-piperidyl)-2,8-bis-(trifluoromethyl)-4-quinolinemethanol, is a known compound and is a valuable active substance for the control of malaria [see e.g. Antimicrobial Agents Chemother. 9, 384 (1976)]. According to the previously known processes, mefloquin has been prepared either via metal-organic intermediate stages [see J. Med. Chem. 14, 926 (1971); German Offenlegungsschriften Nos. 28 06 909 and 29 40 443] or recently with the avoidance of such intermediates according to a process the last step of which comprises catalytically hydrogenating 2-pyridyl-2,8-bis-(trifluoromethyl)-4-quinolyl ketone or 2-pyridyl-2,8-bis-(trifluoromethyl)-4-quinolineacetoxy-methane [see European patent application No. 49 776]. In the foregoing processes there is always obtained, in addition to the erythro form, also a small amount (about 5-15%) of the undesired threo form of the 2-piperidyl-4-quinolinemethanol. The separation of this mixture and the preparation of the pure erythro form has hitherto been possible only by a relatively expensive process involving repeated recrystallization from acetone/alcohol mixtures, washing with acetone and crystallization from acetonitrile.

The present invention provides a synthesis of mefloquin having as few steps as possible and giving mefloquin in high overall yield. In this synthesis, on the one hand, the use of metal-organic intermediate steps is avoided and, on the other hand, in the last stages the mefloquin is formed with high stereo-specificity and is obtained as pure as possible. Therefore, a separation of the threo form from the erythro form of the alpha-(2-piperidyl)-2,8-bis-(trifluoromethyl)-4-quinolinemethanol is not necessary.

More particularly, the problem has been solved in accordance with the present invention by the utilization of the reaction sequence given in the following Reaction Scheme, which proceeds via the two intermediates N-[6-<2,8-bis-(trifluoromethyl)-4-quinolyl>-5-hexenyl]-phthalimide and N-[4-{3-<2,8-bis-(trifluoromethyl)-4-quinolyl>-2-oxiranyl}-butyl]-phthalimide. In this Reaction Scheme I, M is sodium or potassium and X is chlorine, bromine or iodine.

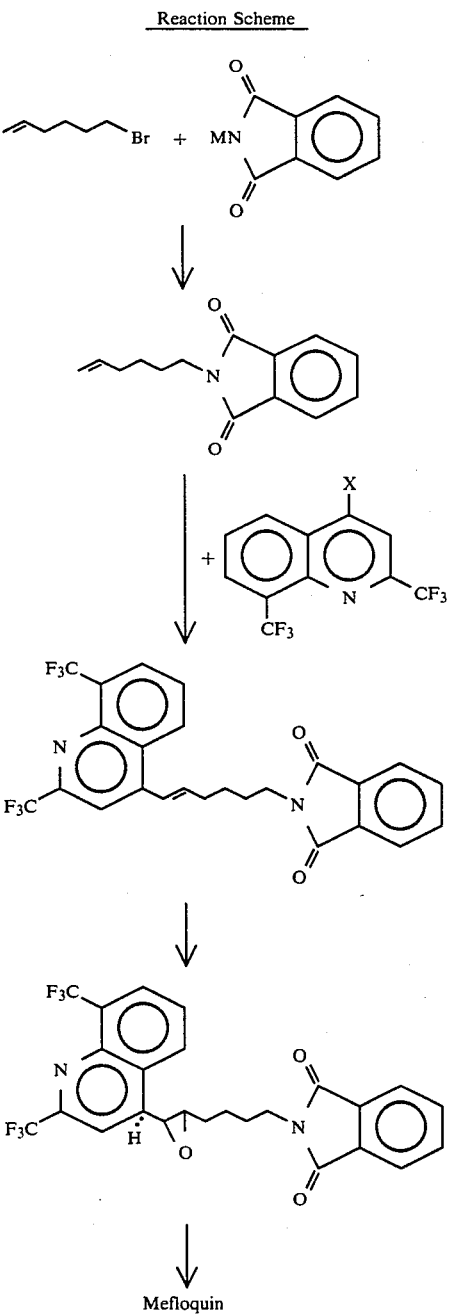

Reaction Scheme

The 6-phthalimido-1-hexene starting material in the foregoing reaction sequence is obtained by reacting a 6-halo-1-hexene, wherein halo is halogen, for example, chlorine, bromine or iodine, preferably 6-bromo-1-hexene, with sodium or potassium phthalimide in a known manner. The reaction is conveniently carried out in the presence of a base, preferably in a basic solvent, for example, N,N-dimethylacetamide.

The 6-phthalimido-1-hexene is then reacted with a 4-halo-2,8-bis-(trifluoromethyl)-quinoline, wherein halo is as described above, to give N-[6-<2,8-bis-(trifluoromethyl)-4-quinolyl>-5-hexenyl]-phthalimide. This reaction is conveniently carried out in an inert organic solvent such as benzene, toluene, acetonitrile, hexamethylphosphortriamide, dimethyl sulfoxide, 1,3- dimethyl-3,4,5,6-tetrahydro-2(1H)-pyrimidinone or 1,3-dimethyl-2-imidazolidinone in the presence of a base, for example, a tertiary alkylamine such as triethylamine or tributylamine, and in the presence of a palladium salt, for example, palladium dichloride or palladium diacetate, and a phosphine, for example, triphenylphosphine or tri-o-tolylphosphine. The fact that the trans product results exclusively in this reaction is the reason for the high mefloquin yield of the reaction sequence in accordance with the invention.

The N-[6-<2,8-bis-(trifluoromethyl)-4-quinolyl>-5-hexenyl]-phthalimide obtained is then epoxidated in an inert solvent to give N-[4-{3-<2,8-bis-(trifluoromethyl)-4-quinolyl>-2-oxiranyl}-butyl]-phthalimide. The epoxidation can be carried out in a known manner with the usual oxidizing agents such as hydrogen peroxide in acetic acid or alkaline solution, peracetic acid, perbenzoic acid, m-chloroperbenzoic acid or tert. butyl hydroperoxide in the presence of a basic catalyst, for example, Triton B (N-Benzyltrimethylammonium hydroxide), in an inert solvent such as dichloromethane, 1,2-dichloroethane, chloroform or tetrahydrofuran.

The conversion, in accordance with the invention, of the N-[4-{3-<2,8-bis-(trifluoromethyl)-4-quinolyl>-2-oxiranyl}-butyl]-phthalimide into mefloquin is carried out by treatment with hydrazine hydrate in an inert solvent, preferably a lower alkanol such as methanol or ethanol, at room temperature to the reflux temperature, preferably while heating to reflux. If the treatment is carried out in the presence of a physiologically compatible acid, then the mefloquin obtained is in the form of the desired acid addition salt. The hydrochloride is the especially preferred acid addition salt. The work-up is conveniently carried out by separating the phthalylhydrazide from the cooled mixture, concentrating the filtrate and treating the residue with an alcohol, for example, methanol, ethanol or isopropanol, preferably methanol, optionally in the presence of 50–80 percent by volume of water. The treatment can be carried out at room temperature or, in order to increase the yield, while cooling to a temperature slightly above 0° C., conveniently for 6-12 hours. The mefloquin hydrochloride, for example, is obtained in this manner in pure form and with almost quantitative yield.

The following Example further illustrates the invention:

EXAMPLE

A suspension of 39 g of potassium phthalimide in 150 ml of N,N-dimethylacetamide was treated at 20° C. while stirring with 27 ml of 6-bromo-1-hexene. After 4 hours, the mixture was poured into 300 ml of ice-water, extracted with ether, the organic phase was washed with 10% sodium chloride solution, dried, filtered and concentrated to dryness. There were obtained 45 g (100%) of 6-phthalimido-1-hexene, m.p. 17°-20° C.

A mixture of 64 g of 4-bromo-2,8-bis-(trifluoromethyl)quinoline, 49 g of 6-phthalimido-1-hexene, 59 ml of tributylamine, 4.5 g of tri-o-tolylphosphine and 1.7 g of palladium diacetate in 300 ml of hexamethylphosphortriamide was heated to 100° C. for 8 hours under argon and while stirring. The mixture was poured into ice-water and extracted with ethyl acetate. The organic phase was washed neutral with water, dried and concentrated to dryness. The crystalline residue was washed with ether. There were obtained 54.9 g (60%) of N-[6-<2,8-bis-(trifluoromethyl)-4-quinolyl>-5-hexenyl]-phthalimide (m.p. 103°-105° C.) in the form of white crystals.

A solution of 35.5 g of N-[6-<2,8-bis-(trifluoromethyl)-4-quinolyl>-5-hexenyl]-phthalimide in 300 ml of chloroform was treated while stirring with 16.5 g of 90% m-chloroperbenzoic acid. The mixture was heated under reflux. After composition of the reaction, excess peracetic acid was decomposed with 10% sodium sulfite solution and the organic phase was extracted with 5% sodium bicarbonate solution, washed with water, dried, filtered and concentrated to dryness. After recrystallization of the residue from dichloromethane/isopropyl ether (2:8; v/v) there were obtained 35.5 g (97%) of N-[4-{3-<2,8-bis-(trifluoromethyl)-4-quinolyl>-2-oxiranyl}butyl]-phthalimide (m.p. 126°-128° C.) in the form of white crystals.

A suspension of 25.4 g of N-[4-{3-<2,8-bis-(trifluoromethyl)-4-quinolyl>-2-oxiranyl}-butyl]-phthalimide in 150 ml of methanol was treated while stirring with 2.65 ml of hydrazine hydrate. The mixture was heated under reflux for 8 hours and then concentrated under reduced pressure. The crystalline residue was suspended in ethanol and the suspension, after the addition of 11 ml of a 5N ethanolic hydrogen chloride solution, was heated under reflux for 1 hour. After cooling, the phthalylhydrazide was filtered under suction. The filtrate was concentrated and the crystalline residue was recrystallized from ethanol. There were obtained 19 g (96%) of mefloquin hydrochloride (m.p. 254°-256° C.) in the form of white crystals.

I claim:
1. N-[4-{3-<2,8-Bis-(trifluoromethyl)-4-quinolyl>-2-oxiranyl}-butyl]-phthalimide.
2. N-[6-<2,8-Bis-(trifluoromethyl)-4-quinolyl>-5-hexenyl]-phthalimide.

* * * * *